US012337070B1

(12) United States Patent
Doyle et al.

(10) Patent No.: US 12,337,070 B1
(45) Date of Patent: Jun. 24, 2025

(54) DEVICES FOR DISINFECTING A SURFACE USING ULTRAVIOLET LIGHT

(71) Applicant: The United States of America as represented by the Secretary of the Navy, Arlington, VA (US)

(72) Inventors: Christopher S. Doyle, Bremerton, WA (US); Branden L. Doyle, Gig Harbor, WA (US); Wilson H. Davenport, Port Orchard, WA (US)

(73) Assignee: The United States of America as represented by the Secretary of the Navy, Keyport, WA (US)

( * ) Notice: Subject to any disclaimer, the term of this patent is extended or adjusted under 35 U.S.C. 154(b) by 894 days.

(21) Appl. No.: 17/336,091

(22) Filed: Jun. 1, 2021

Related U.S. Application Data

(60) Provisional application No. 63/102,221, filed on Jun. 1, 2020.

(51) Int. Cl.
*A61L 2/10* (2006.01)
*G02B 5/08* (2006.01)
(Continued)

(52) U.S. Cl.
CPC .............. *A61L 2/10* (2013.01); *G02B 5/0891* (2013.01); *H05B 45/10* (2020.01); *H05B 47/16* (2020.01);
(Continued)

(58) Field of Classification Search
CPC ..... A61L 2/10; A61L 2202/11; G02B 5/0891; H05B 45/10; H05B 47/16; H05K 7/20145
See application file for complete search history.

(56) References Cited

U.S. PATENT DOCUMENTS 7,226,187 B2    6/2007   Yamazaki et al.
8,142,715 B2    3/2012   Curry et al.
(Continued)

OTHER PUBLICATIONS

Rozenberg et al., Can We Use Adenovirus Validated Ultraviolet Systems for Inactivation of SARS-CoV-2, The Virus That Causes COVID-19?; Atlantium Tech.; Prior to Jun. 1, 2020.
(Continued)

*Primary Examiner* — Sean E Conley
*Assistant Examiner* — Brendan A Hensel
(74) *Attorney, Agent, or Firm* — Stephen J. Leahu; Naval Undersea Warfare Center, Keyport

(57) ABSTRACT

A device and method for disinfecting a surface. The device including a frame; a power source connected to the frame; an ultraviolet light emitting array of light emitting diodes connected to the frame and electrically connected to the power source; and a beam forming reflector connected to the light emitting array to reflect the ultraviolet light to the surface to be disinfected, the beam forming reflector having two opposing walls on opposite sides of at least one of the light emitting diodes, each of the two opposing walls extending away from the one light emitting diode in a divergent manner relative to each other such that each of the two opposing walls form a side of an acute angle and, together, the two opposing walls form a light passageway through which the ultraviolet light passes while traveling towards the surface to be disinfected, the acute angle configuration of the two opposing walls widening the light passageway as the light passageway becomes further removed from the one light emitting diode, the two opposing walls being coated with sintered polytetrafluoroethylene, wherein the reflectivity of the beam forming complex exceeds 90% reflectivity of the ultraviolet light emitted by the one light emitting diode.

16 Claims, 14 Drawing Sheets

(51) Int. Cl.
  *H05B 45/10* (2020.01)
  *H05B 47/16* (2020.01)
  *H05K 7/20* (2006.01)
(52) U.S. Cl.
  CPC ...... *H05K 7/20145* (2013.01); *A61L 2202/11* (2013.01)

(56) References Cited

U.S. PATENT DOCUMENTS

| | | | |
|---|---|---|---|
| 8,415,647 | B2 | 4/2013 | Hartung |
| 9,265,850 | B2 | 2/2016 | Davis et al. |
| 10,730,072 | B2 | 8/2020 | Wang et al. |
| 10,994,040 | B2 | 5/2021 | Kennedy et al. |
| 2014/0161664 | A1* | 6/2014 | Harris .................. A61L 2/084 250/454.11 |
| 2015/0129776 | A1* | 5/2015 | Boodaghians .......... C02F 1/325 250/432 R |
| 2019/0105415 | A1* | 4/2019 | Gross .................. A61L 2/10 |
| 2019/0142981 | A1* | 5/2019 | Kim .................. A61L 2/10 250/455.11 |
| 2019/0338919 | A1* | 11/2019 | Wilk .................. F21V 7/0016 |

OTHER PUBLICATIONS

Woo et al.; Efficacy of Inactivation of Human Enteroviruses by Dual-Wavelength Germicidal Ultraviolet (UV-C) Light Emitting Diodes (LEDs); Water; May 30, 2019.
Dai et al.; Ultraviolet C irradiation: an alternative antimicrobial approach to localized infections?; NIH Public Access; Feb. 2012.
GermAwayUV Premier 35 Watt Handheld UVC Surface Sanitzer Scrubber; CureUV.com; Prior to Jun. 1, 2020.
OmniCure UV Curing Product Catalog; Excelitas Technologies; 2019.
Porex LED Reflectors: High-Performance Diffuse Reflectors Brochure; Porex Filtration Group; 2018.
Sintered PTFE; https://porex.com/porous-polymers-technology/sintered-porous-plastic/sintered-ptfe/; Porex Filtration Group; Prior to Jun. 1, 2020.

* cited by examiner

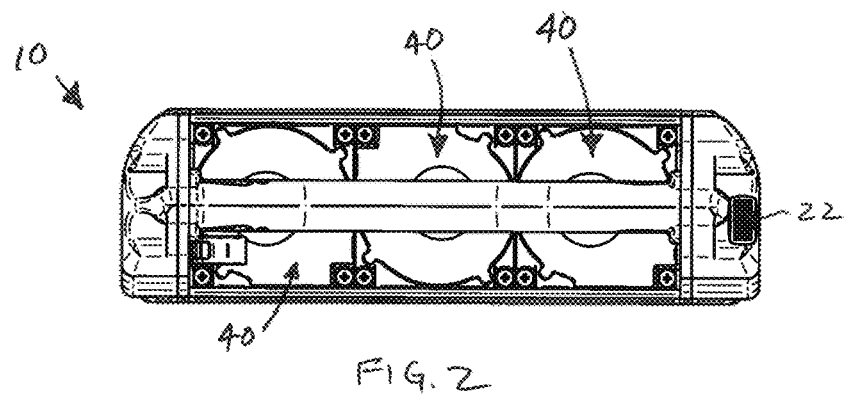
FIG. 2
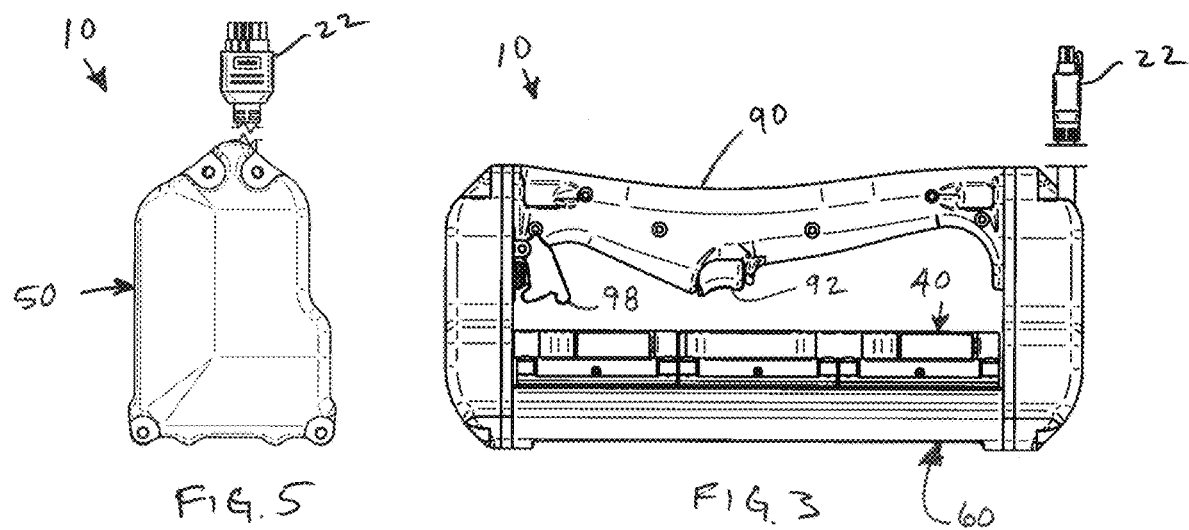
FIG. 5
FIG. 3
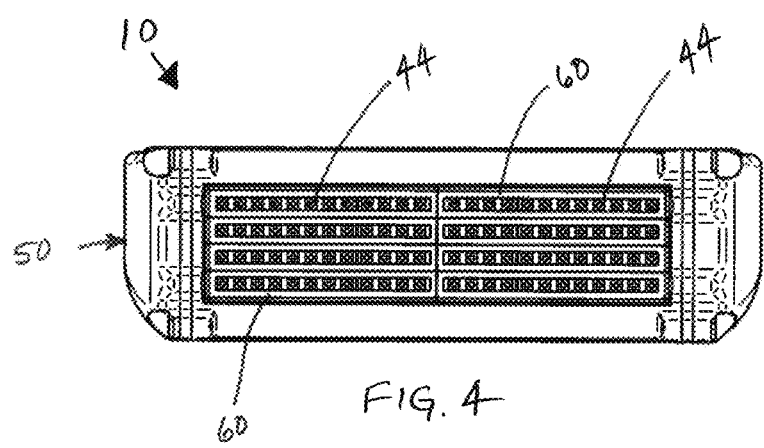
FIG. 4

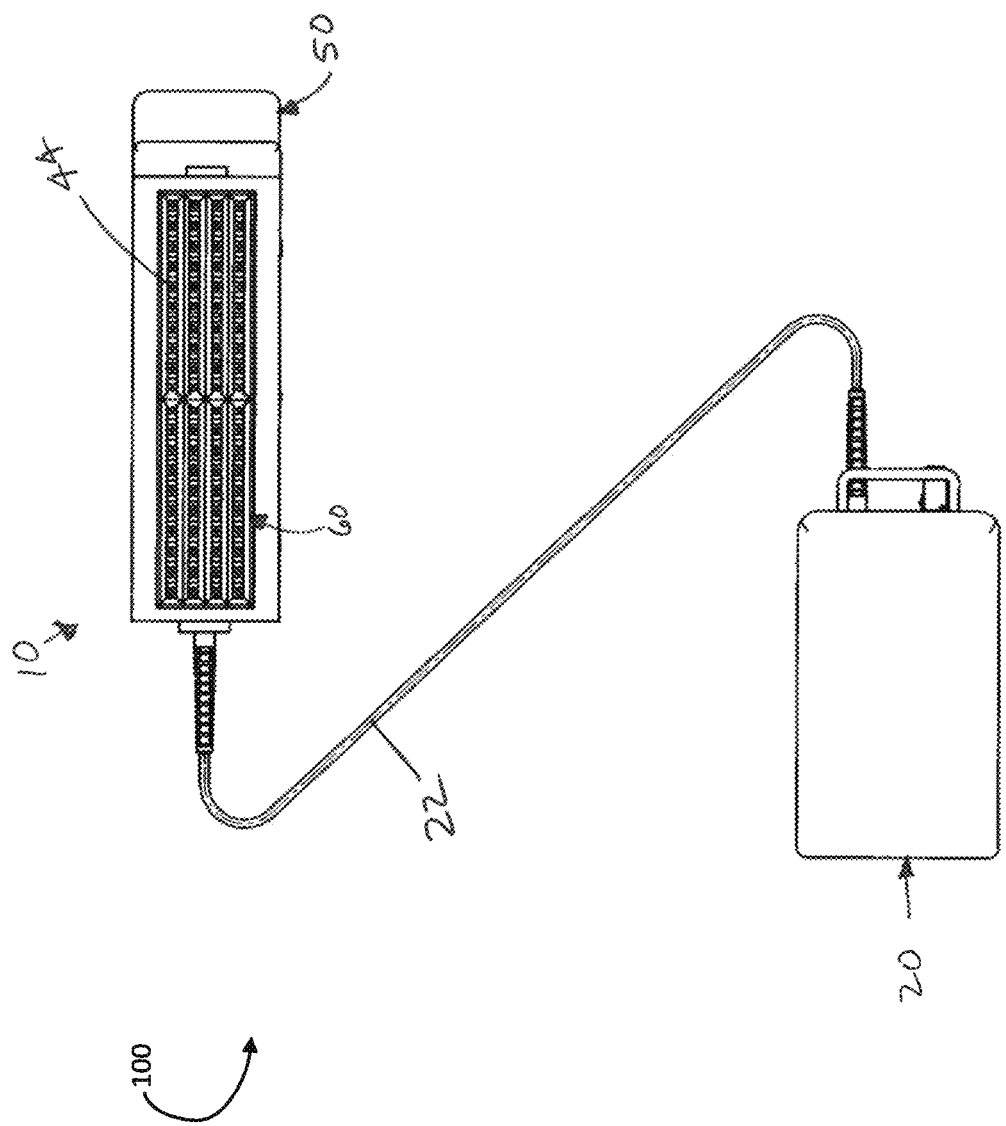

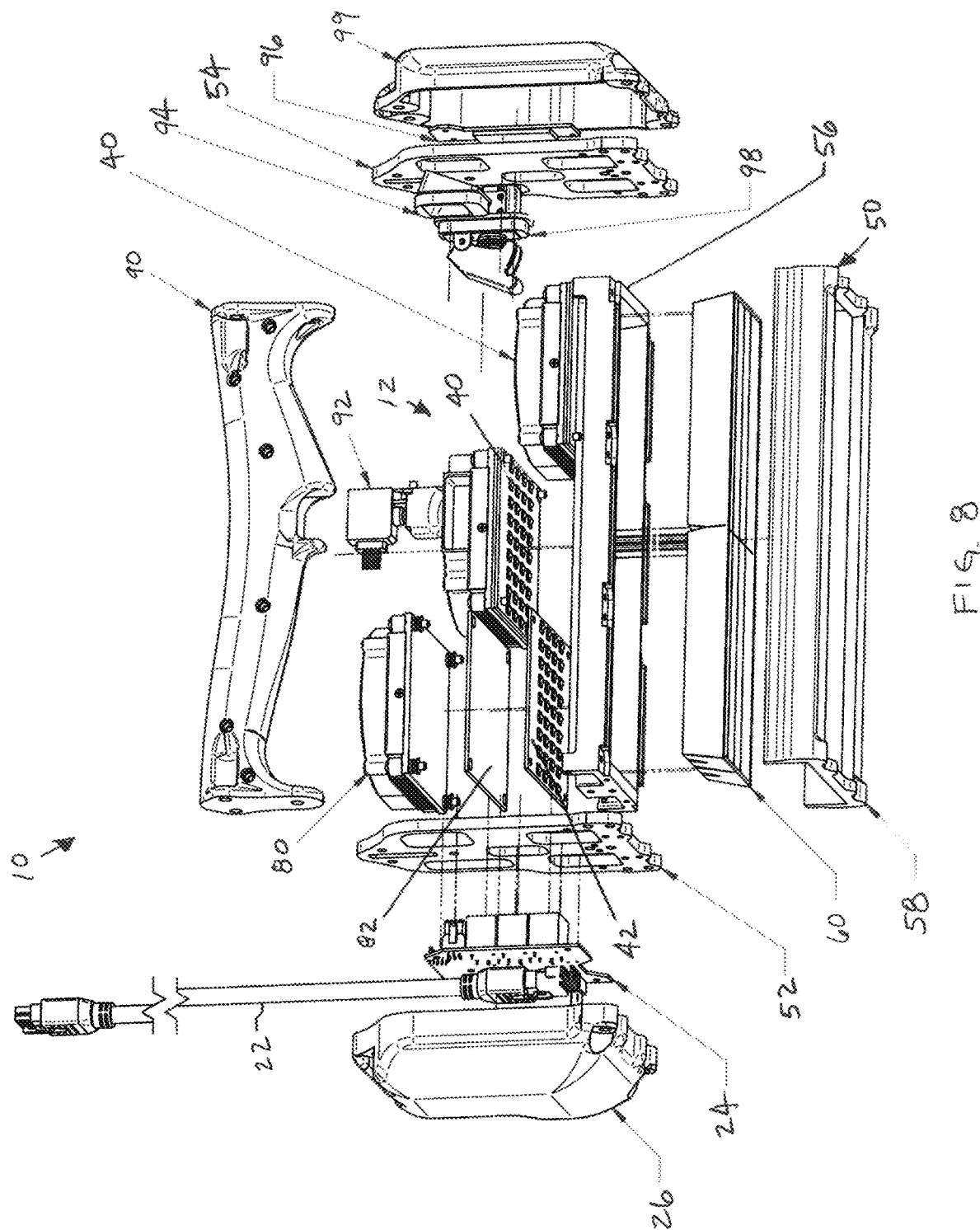

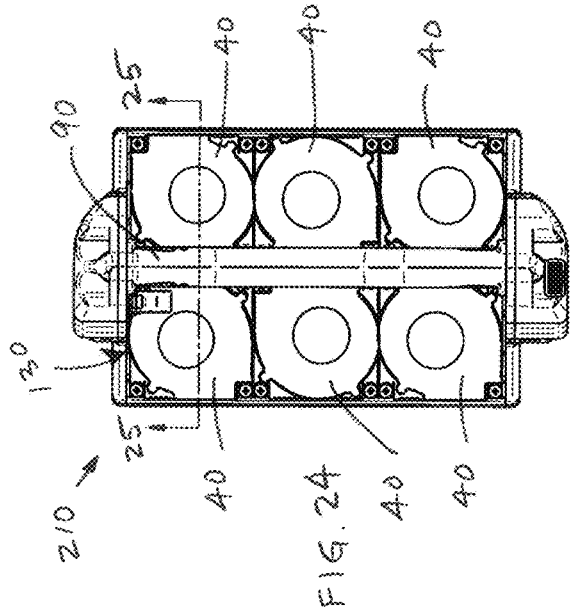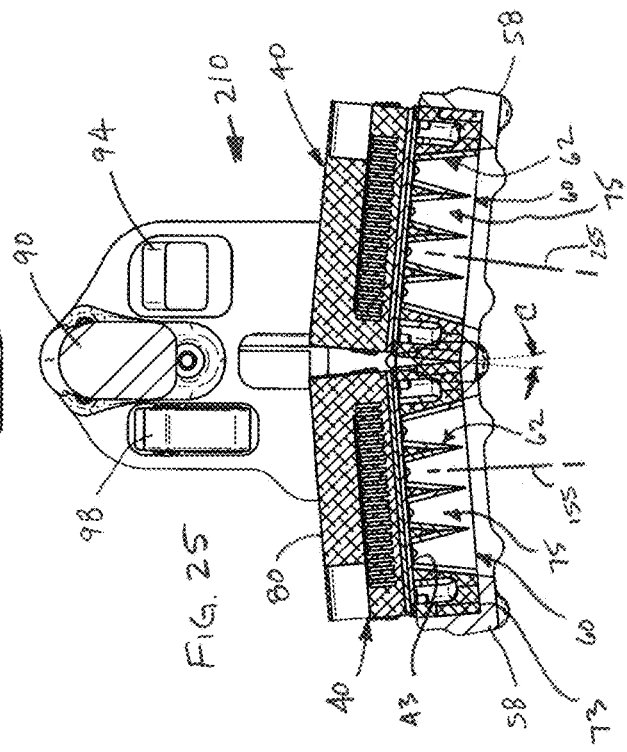

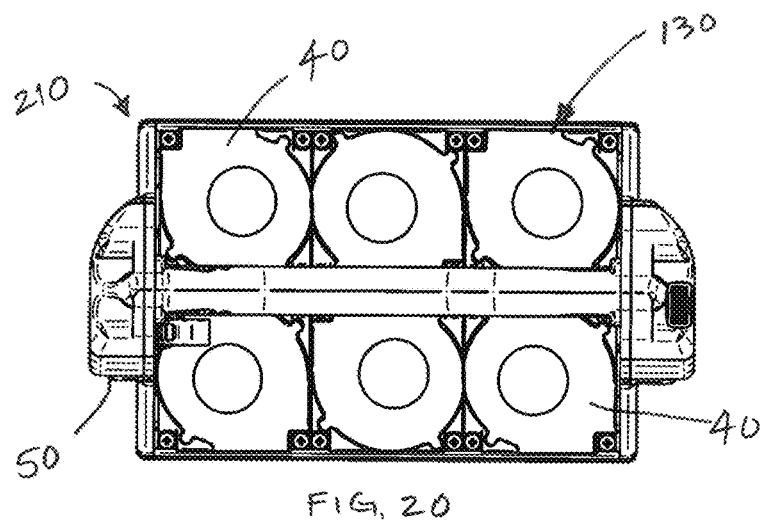
FIG. 20
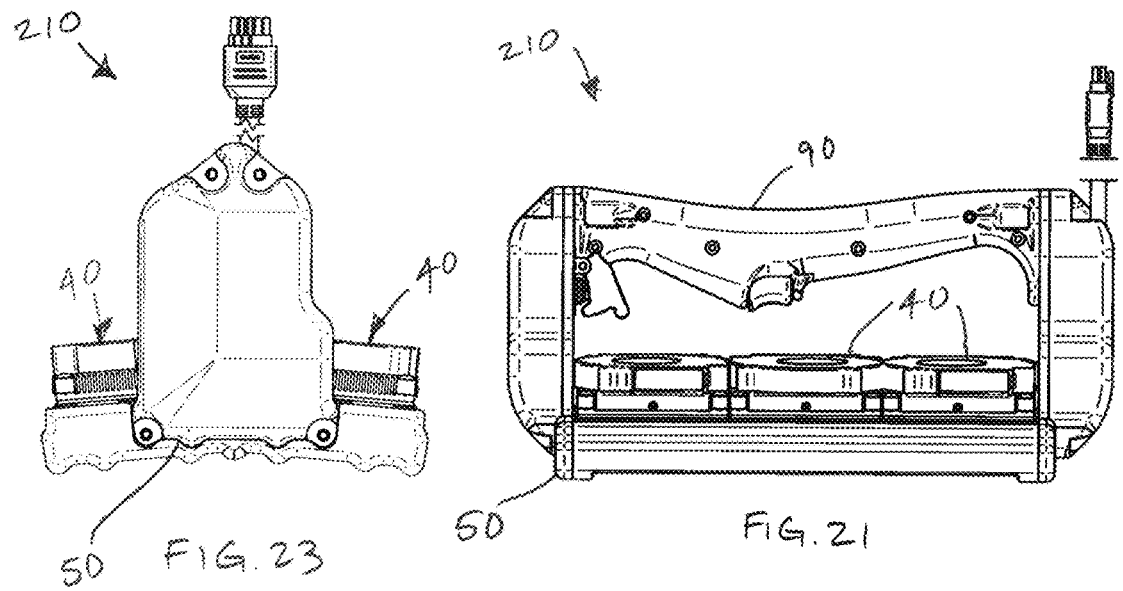
FIG. 23
FIG. 21
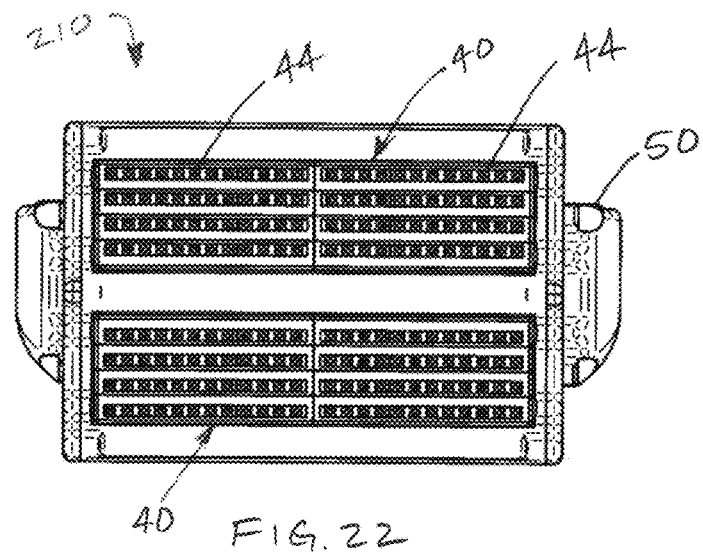
FIG. 22

DEVICES FOR DISINFECTING A SURFACE USING ULTRAVIOLET LIGHT

CROSS REFERENCE TO OTHER PATENT APPLICATIONS

The present application claims the benefit of U.S. provisional patent application 63/102,221 filed 1 Jun. 2020 and titled: Ultraviolet LED Viral, Bacterial, Fungal Inactivation System Emitter, the complete disclosure of which is incorporated herein by reference.

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to a device and method for disinfecting surfaces that harbor biological agents such as viruses, bacteria, fungus, and mold by emitting ultraviolet radiation from the device onto the surface.

Mercury arc lamp emitters, pulsed Xenon arc lamps, and LED emitters are known in the art for emitting ultraviolet light for disinfecting surfaces. However, mercury arc lamp emitters are limited in the ability to provide a uniform, stable, and consistent radiation emission. Additionally, the mercury UV lamps use aluminum reflectors which are limited to relatively low reflectance of less than 80 percent reflective in practical applications. The major disadvantages of mercury arc lamp emitters are the use of elemental mercury which poses environmental and health concerns during disposal and in the event of lamp breakage. Pulsed Xenon arc lamps are limited because the beam/emission is difficult to characterize. Additionally, the hardware and power requirements of pulsed Xenon emitters leads to complications when considering for handheld use. Prior art LED ultraviolet emitters that are configured for inactivation of biological agents are limited by unit emission intensity, size, or the unit cost is prohibitive.

U.S. Pat. No. 7,626,187 to Younts, incorporated herein by reference, discloses a method and apparatus intended for eradicating undesirable elements that cause disease, ailments or discomfort.

U.S. Pat. No. 8,142,715 to Curry et alt, incorporated herein by reference, discloses a method and apparatus for ultraviolet decontamination of surfaces.

U.S. Pat. No. 8,415,647 to Hartung, incorporated herein by reference, discloses an irradiation appliance.

U.S. Pat. No. 9,265,850 to Davis et al., incorporated herein by reference, discloses an ultraviolet sanitizer with a wand.

U.S. Pat. No. 10,730,072 to Wang et al., incorporated herein by reference, discloses dispensing and ultraviolet curing with low backscatter.

U.S. Pat. No. 10,994,040 to Kennedy et al., incorporated herein by reference, discloses a surface treatment with ultraviolet light.

SUMMARY OF THE INVENTION

In view of the shortcomings of the prior art, one aspect of the invention is to provide a device for disinfecting a surface, comprising a frame; a power source connected to the frame; an ultraviolet light emitting array of light emitting diodes connected to the frame and electrically connected to the power source; and a beam forming reflector connected to the light emitting array to reflect the ultraviolet light to the surface to be disinfected, the beam forming reflector having two opposing walls on opposite sides of at least one of the light emitting diodes, each of the two opposing walls extending away from the one light emitting diode in a divergent manner relative to each other such that each of the two opposing walls form a side of an acute angle and, together, the two opposing walls form a light passageway through which the ultraviolet light passes while traveling towards the surface to be disinfected, the acute angle configuration of the two opposing walls widening the light passageway as the light passageway becomes further removed from the one light emitting diode, the two opposing walls being coated with sintered polytetrafluoroethylene, wherein the reflectivity of the beam forming complex exceeds 90% reflectivity of the ultraviolet light emitted by the one light emitting diode.

According to another aspect of the invention, the invention provides a device for disinfecting a surface, comprising: a frame; a power source connected to the frame; first and second ultraviolet light emitting arrays of light emitting diodes connected to the frame and electrically connected to the power source, the first array of light emitting diodes being positioned on a first support that presents the light emitting diodes on a first plane and the second array of light emitting diodes being positioned on a second support that presents the light emitting diodes on a second plane; and a first beam forming reflector connected to the first light emitting array and a second beam forming reflector connected to the second light emitting array, each of the first and second beam forming reflectors connected to its respective the light emitting array to reflect the ultraviolet light to the surface to be disinfected, each the beam forming reflector having two opposing walls on opposite sides of at least one of the light emitting diodes, each of the two opposing walls extending away from the one light emitting diode in a divergent manner relative to each other such that each of the two opposing walls form a side of an acute angle and, together, the two opposing walls form a light passageway through which the ultraviolet light passes while traveling towards the surface to be disinfected, the acute angle configuration of the two opposing walls widening the light passageway as the light passageway becomes further removed from the one light emitting diode, the first and second light emitting arrays being connected to the frame such that the first plane forms an acute angle with the second plane such that a first line normal to the first plane will converge with a second line normal to the second plane.

According to another aspect of the invention, the invention provides a method for disinfecting a surface, comprising the steps of: providing a device for disinfecting a surface, the device including a frame, a power source connected to the frame, a first ultraviolet light emitting array of light emitting diodes removably connected to the frame in a first position and electrically connected to the power source, the first array of light emitting diodes being positioned on a first support that presents the light emitting diodes on a first plane, and a first beam forming reflector connected to the first light emitting array to reflect ultraviolet light to the surface to be disinfected; activating the first ultraviolet light emitting array to disinfect a surface with ultraviolet light; deactivating the device after a period of time; disconnecting the first ultraviolet light emitting array from the frame; reconnecting the first ultraviolet light emitting array on the fame in a second position, providing a second ultraviolet light emitting array of light emitting diodes removably connected to the frame in a third position and electrically connected to the power source, the second array of light emitting diodes being positioned on a second support that presents the light emitting diodes on a second plane, and a second beam forming reflector connected to the second light emitting array to reflect ultraviolet light to the surface to be disinfected, and activating the first and second ultraviolet light emitting arrays to disinfect a surface with ultraviolet light.

Further advantages and features of the present invention will be described in detail below.

BRIEF DESCRIPTION OF THE DRAWINGS

The present invention will now be described, by way of example, with reference to the accompanying drawings, wherein like numbers indicate same or similar parts or components, and wherein

FIG. 2 illustrates a top view of the device in accordance with an embodiment of the invention;

FIG. 3 illustrates a side view of the device in accordance with an embodiment of the invention;

FIG. 4 illustrates a bottom view of the device in accordance with an embodiment of the invention;

FIG. 5 illustrates an end view of the device in accordance with an embodiment of the invention;

FIG. 6 illustrates a bottom view of the device, including a bottom view of a power supply in accordance with an embodiment of the invention;

FIG. 8 illustrates an exploded view of the device in accordance with an embodiment of the invention;

FIG. 16 illustrates a top view, similar to FIG. 2, of the device in accordance with an embodiment of the invention;

FIG. 17 illustrates a cross-sectional view taken along line 17-17 in FIG. 16;

FIG. 20 illustrates a top view of the device in accordance with a second embodiment of the invention;

FIG. 21 illustrates a side view of the device in accordance with a second embodiment of the invention;

FIG. 22 illustrates a bottom view of the device in accordance with a second embodiment of the invention;

FIG. 23 illustrates an end view of the device in accordance with a second embodiment of the invention;

FIG. 24 illustrates a top view of the device in accordance with a second embodiment of the invention;

FIG. 25 illustrates a cross-sectional view taken along line 25-25 in FIG. 24;

DESCRIPTION OF EXEMPLARARY EMBODIMENTS OF THE INVENTION

Figure 1:
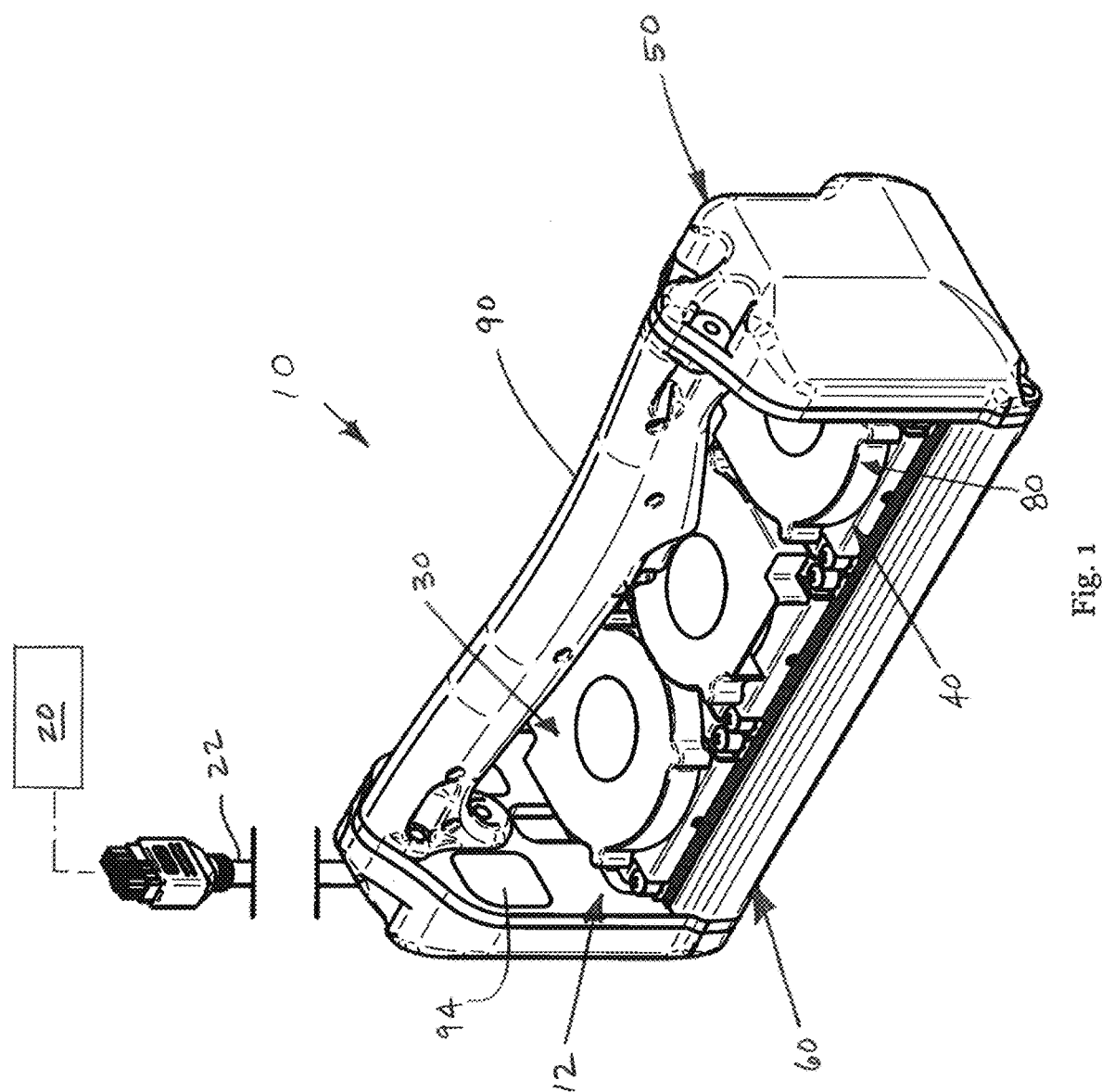
FIG. 1 illustrates a top-side perspective view of the device, including a power supply illustrated schematically, in accordance with an embodiment of the invention.
Figure 7:
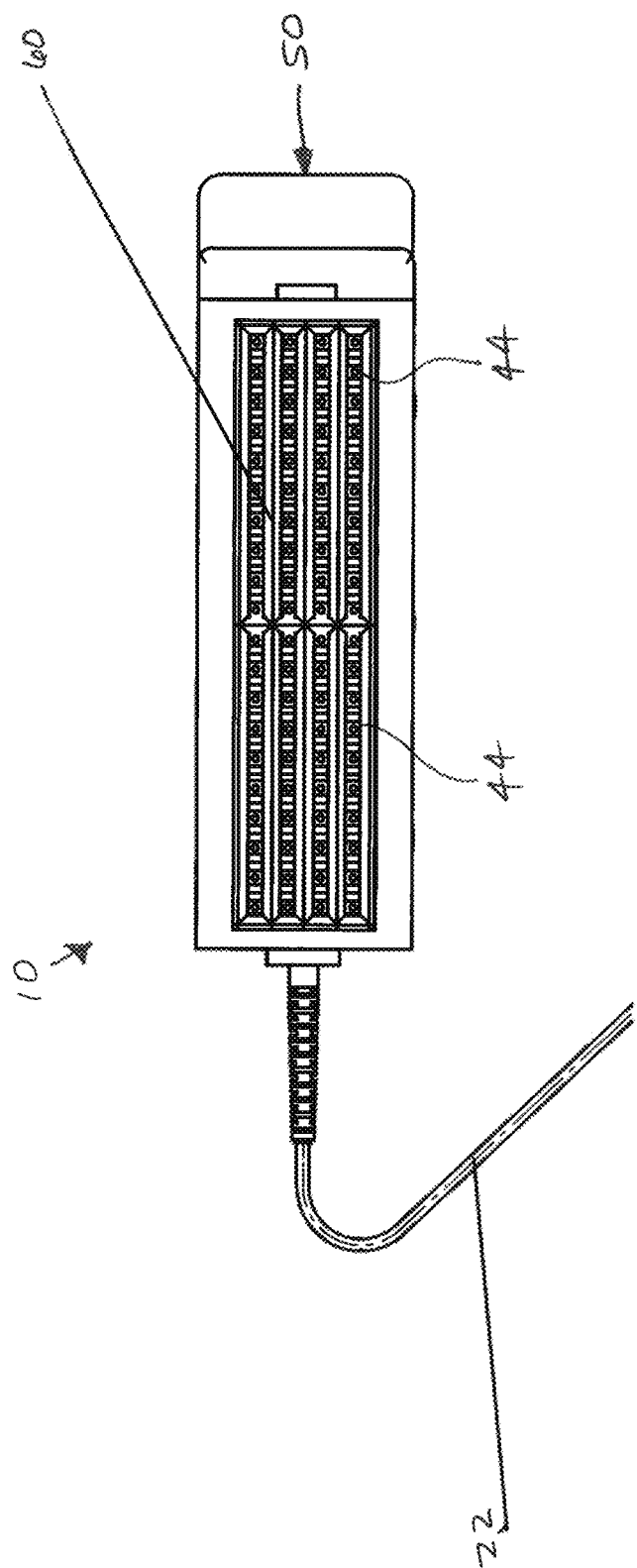
FIG. 7 is an enlarged bottom view of the device similar to FIG. 6 in accordance with an embodiment of the invention, but not showing the power supply.
Figure 10:
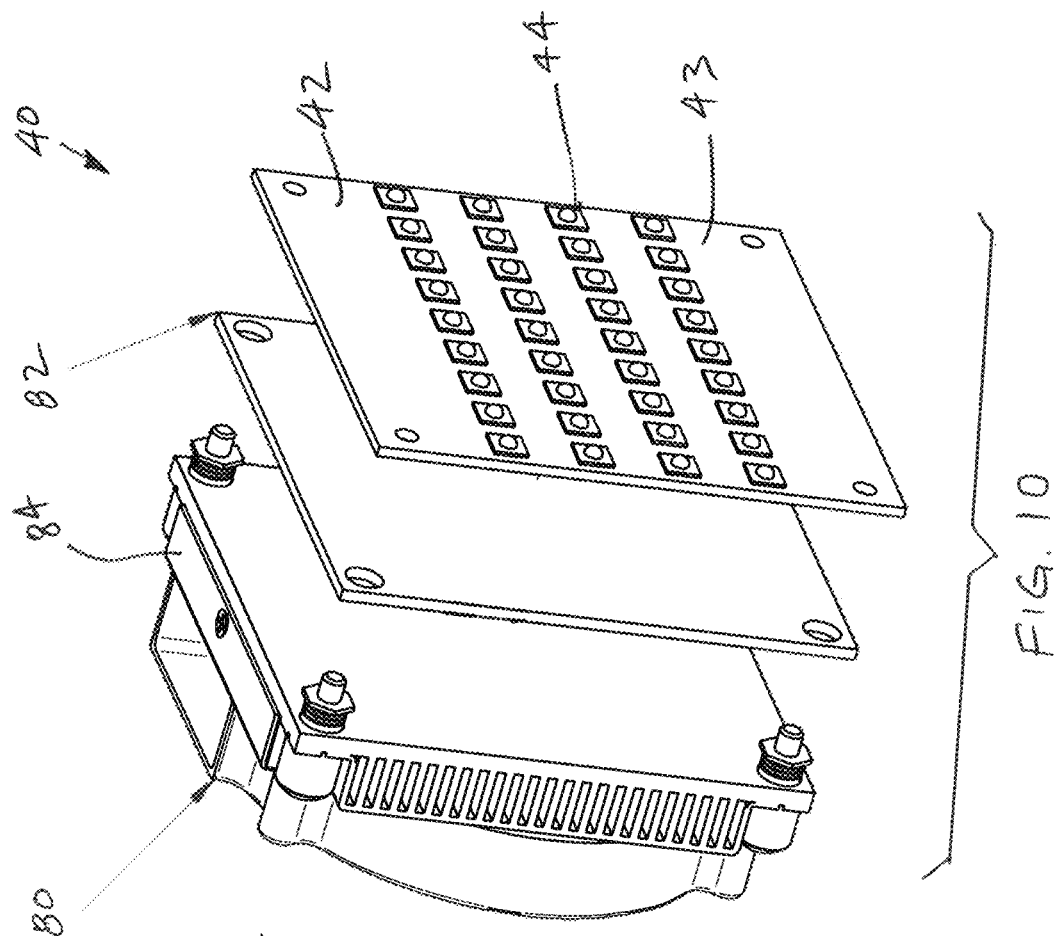
FIG. 10 illustrates an exploded perspective view of the emitter array illustrated in FIG. 9.
Figure 9:
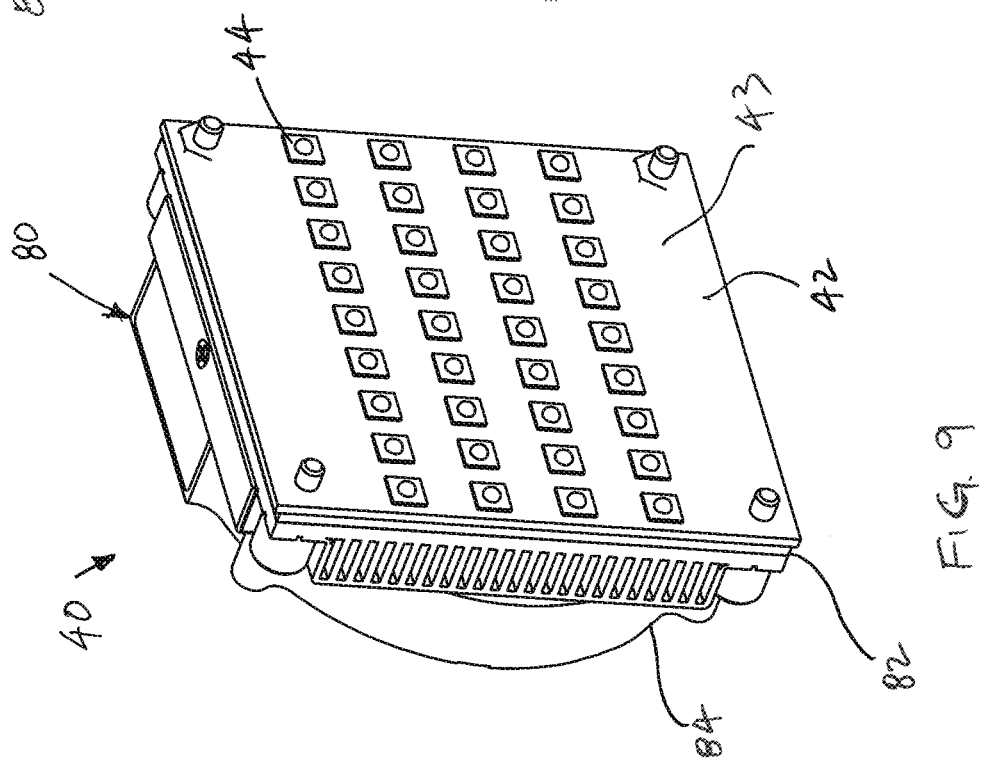
FIG. 9 illustrates a bottom-side perspective view of the emitter array of the device in accordance with an embodiment of the invention.
Figure 12:
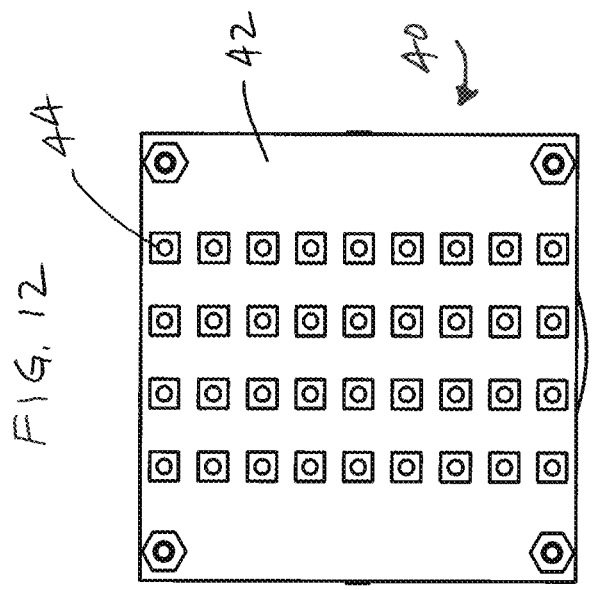
FIG. 12 illustrates a bottom view of the emitter array illustrated in FIG. 9.
Figure 13:
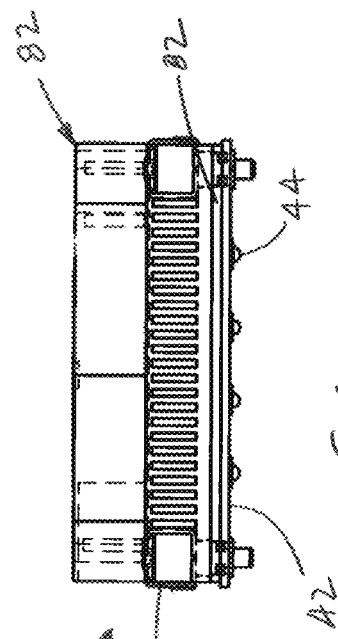
FIG. 13 illustrates a side view of the emitter array illustrated in FIG. 9.
Figure 11:
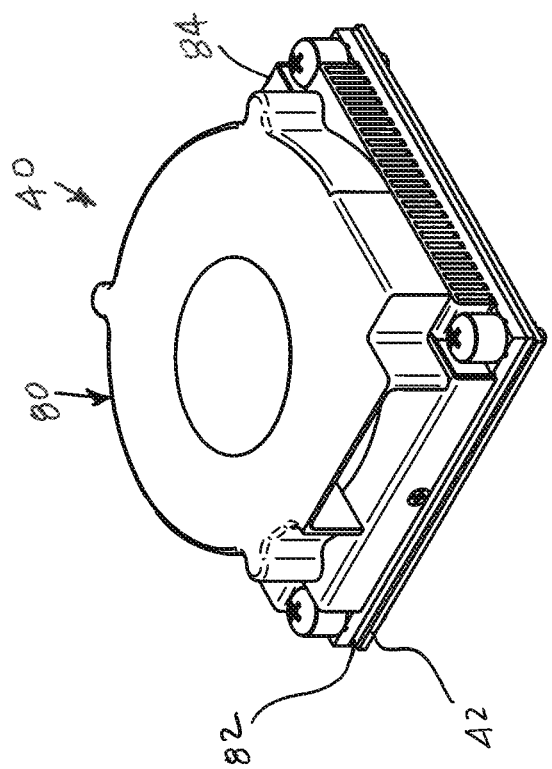
FIG. 11 illustrates a top-side perspective view of the emitter array illustrated in FIG. 9.
Figure 14:
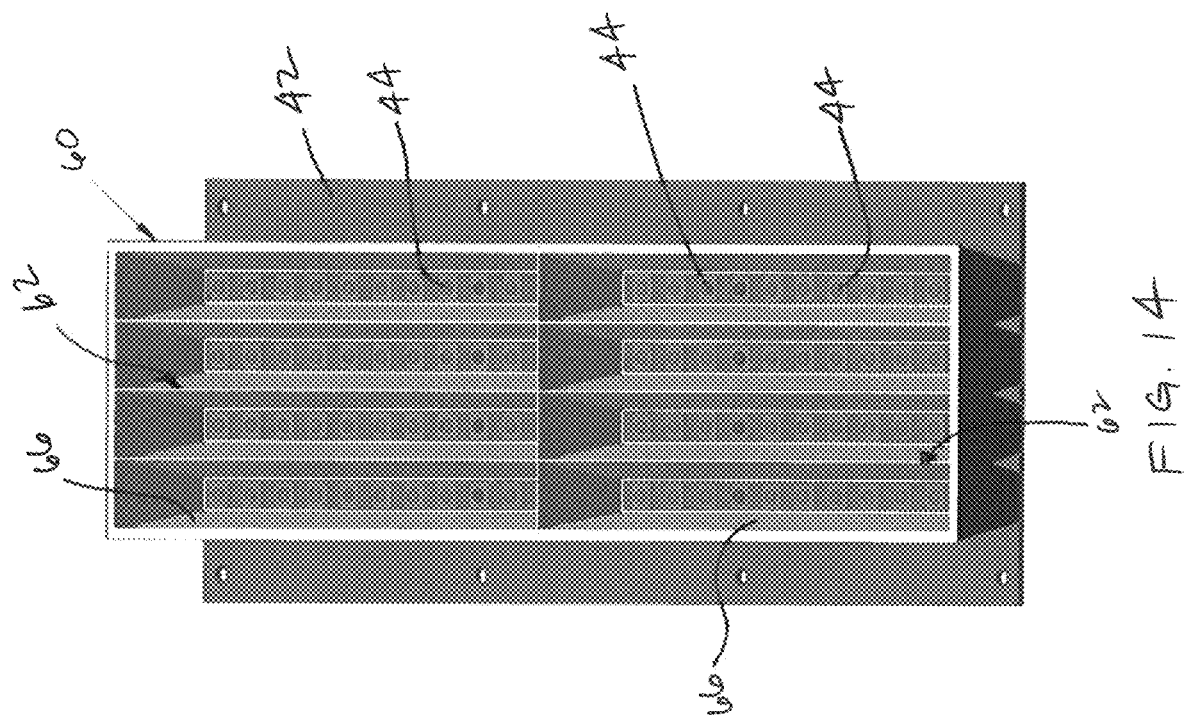
FIG. 14 illustrates a bottom-side perspective view of a beam forming complex in accordance with an embodiment of the invention.

One embodiment of the invention is most principally a handheld unit 10 capable of emitting a controllable emission of ultraviolet radiation on to a surface in a consistent and directed radiation field. One use of the unit 10 is for sterilization of surfaces that are suspected to harbor infections biological agents.

As seen in FIGS. 1-13, in a first embodiment of the invention, the unit 10 includes the handheld ultraviolet (UV) radiation emitter 12, which is attached to an appropriate power supply 20. The handheld UV radiation emitter 12 includes an ultraviolet emitter array assembly 30 comprised of multiple array modules 40. The array assembly 30 is mounted within frame 50, which additionally houses a radiation beam forming complex 60 and provides space for internally running any cables and wiring necessary for the array assembly 30.

Each array module 40 includes a thermal management system 80, which forms the top of the array module 40. Handle 90 is attached to the frame 50. Handle 90 functions as the operator-to-machine interface; the operator uses the handle 90 to hold and control the unit 10, including to fire the emitter 12 via a finger trigger 92 in order to emit ultraviolet radiation. The handle 90 additionally functions as the main housing for the power distribution, emitter firing control, and system diagnostics/status componentry (including the display screen 94 and microcontroller 96), as will be further described herein. A power cable 22 projects from the unit handle 90 and supplies low voltage power to the unit 10. The power cable 22 extends into the power supply 20, which converts AC electrical power to DC electrical power.

The emitter array 30 includes multiple array modules 40. Each array module 40 includes a metal core printed circuited board (MCPCB) 42, which houses individual light emitting diodes 44 (LED) preferably emitting type-C ultraviolet light, the copper circuitry that powers each LED emitter 44 and the known LED driver componentry. The MCPCB 42 additionally serves as a thermal management component by transferring thermal energy from the LED emitters 44 into the main thermal management system 80. All the array modules 40 are interconnected via known LED driver componentry for the function of array emission balancing.

The unit frame 50 is the backing structure for the beam forming complex 60, which is the component that directs the ultraviolet radiation from the LED emitters 44 into a consistent, even and usable emission and onto the surface for treatment of the surface.

The thermal management system 80 is comprised of a known thermal substrate 82 and a heat exchanger 84, which may include a cooling fan and thermal monitoring sensors, all of which function to remove and monitor excess thermal energy generated by the LED emitters 44 as is known.

The unit handle 90 provide the manner in which a user holds the unit 10 and fires the array assembly 30 via the trigger 92. The unit handle also houses the array assembly power distribution board, which centrally distributes electricity to each of the array modules 40 in a known manner. The handle 90 holds the system control and diagnostics microcontroller 96, which controls the array assembly 30 firing via a signal from the trigger 92 and monitors the system for parameters such as LED emitter 44 temperature, as is generally known. System status will be displayed via a known display 94 mounted into the handle 90.

The power supply 20 is generally known and would typically include a power supply unit (PSU), a master arm switch 98, and a power supply case. The known PSU converts AC electricity into low voltage DC electricity (<30 VDC). A master arm switch 98 may be used in a known way to energize the entire system and act as a protection to inadvertently firing the unit 10 in the event the trigger 92 was accidently pulled.

When operating in a preferred manner, the operator would identify a surface that requires sterilization. The unit 10 and the power supply 20 are transported to the subject location. The operator would connect the power supply 20 to a standard 120 VAC wall outlet. The operator would typically don the appropriate personal protective equipment when applicable. The operator would then toggle the master arm switch 98 at which time the unit would indicate that the emitter unit 10 is armed and ready for use. The operator will then pick up the emitter unit 10 via the handle 90 and dwell over the area to be sterilized. Once the trigger 92 is pulled the unit will audibly and visually indicate to the operator that the emitter array assembly 30 is firing. The operator will move the unit 10 over the surface needing sterilization until the desired dose is achieved. Once the desired dose is achieved, the operator will release the trigger 92, turning off the emitter array assembly 30. Once the emitter array assembly 30 is off following surface sterilization, the display screen 94 will display the sterilization time and system status so that the operator can observe dose time via the display. If finished with sterilization, the operator disarms the unit by toggling the master arm switch 98 into the off position and stows the unit 10. Because the device emitters are LED emitters 44, the size and weight of the whole system is less than a comparable system formed with other known sources of ultraviolet light, such as pulse xenon arc systems. Additionally, due to the solid-state nature of the LED emitters 44, the device 10 has a high durability respectively to prior art systems that implement glass arc bulbs.

FIG. 8 provides an exploded view of unit 10, illustrating the handle 90, power supply cable 22, display screen 94, power module 24, finger trigger 92, thermal management system 80, thermal interface material substrate 82, ultraviolet radiation array module 40, metal core printed circuited board 42, beam forming complex 60, unit master arm switch 98, power module cover 26, and control system cover 99 enclosing the microcontroller 96. The frame 50 includes frame side panels 52 and 54, a frame top 56, and a frame bottom 58.

Finger trigger 92 slots into the underside of handle 90, which attaches to the top of side panels 52 and 54 in a known manner. Just below handle 90, each thermal management system 80 rests upon a thermal substrate 82 and a circuit board 42 with LED emitters 44. Thermal substrate 82 may be various types of known heat transferring assisting materials. Alternatively, the LED emitters 44 can be mounted directly to the heat sink eliminating the need for the circuit board 42. This may improve the thermal performance of thermal management system 80 by eliminating components from the thermal resistance network. In the embodiment shown, each ultraviolet radiation array module 40 has a thermal management system 80. Each ultraviolet array module 40, including the metal core printed circuited board 42 and the thermal management system 80, are coupled in a known manner onto the frame top 56. Beam forming complex 60 slots into the frame top 56 from beneath. Frame top 56 connects to side panels 52 and 54. Frame bottom 58 attaches over the bottom of frame top 56, enclosing, there between, the beam forming complex 60. Display screen 94 and unit master arm switch 98 mount to side panel 54. Power module 24 mounts to side panel 52. Power supply cable 22 exits from the top of power module 24. Power cable 22 attaches to power supply 20 (not illustrated in FIG. 8). Power module cover 26 encloses power module 24 and the outside of side panel 52. Control system cover 99 is attached to the outside of side panel 54.

Figure 15:
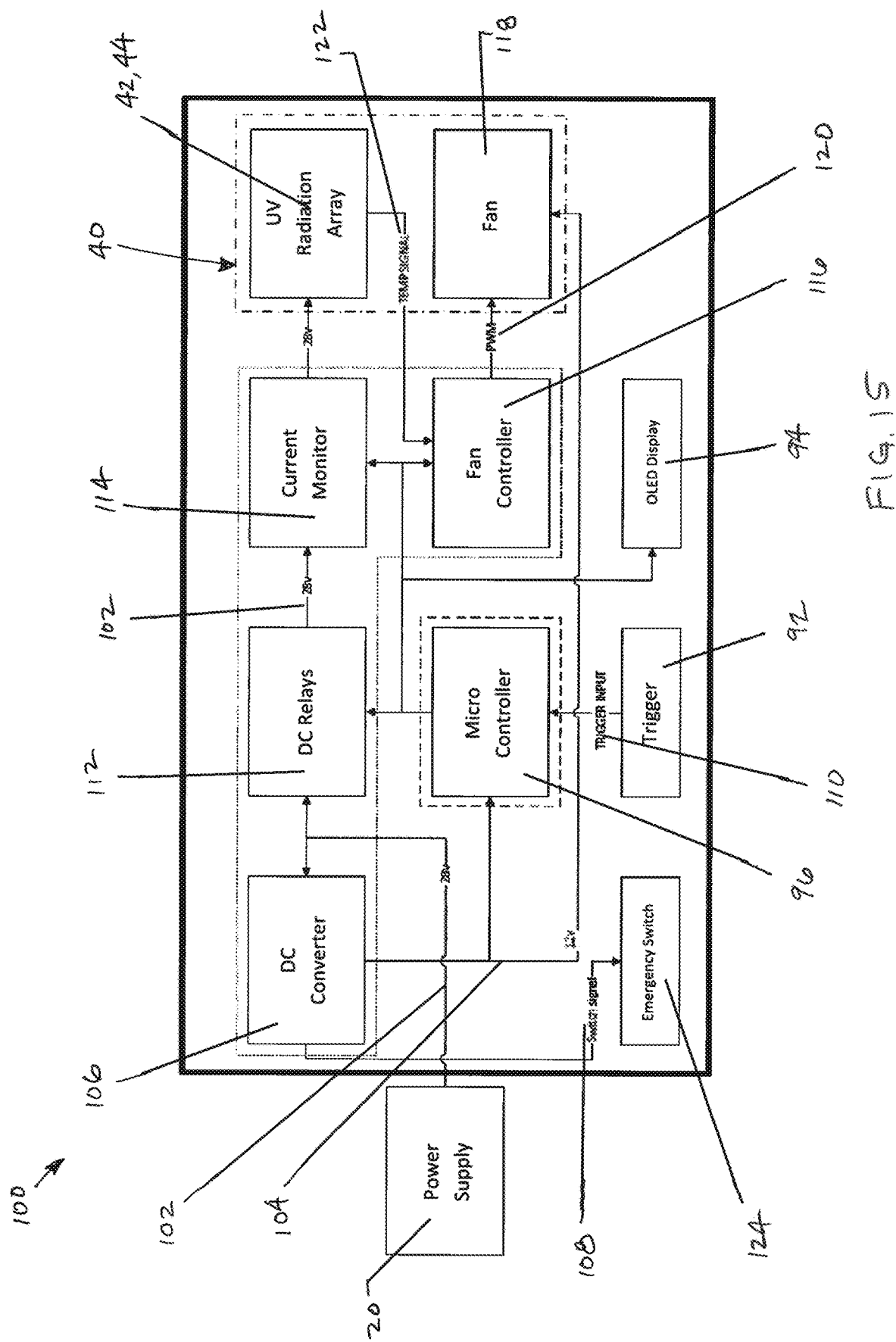
FIG. 15 illustrates a block diagram of internal electrical components of the invention according to an embodiment of the invention.

FIG. 15 is a block diagram of one embodiment of the electrical system 100 for unit 10, including power supply 20, DC voltage 102, converted voltage 104, DC converter 106, micro controller 96, switch signal 108, emergency switch 124, finger trigger 92, trigger input 110, DC relays 112, current monitor 114, fan controller 116, fan 118, pulse width modulation 120, array module 40, an ultraviolet radiation array formed by the printed circuit board 42 and the LED emitters 44, temperature signal 122, and display 94, which may be an organic light emitting diode display (OLED).

Power enters power supply 20, which converts AC electricity, usually from a 128 volt wall outlet, to a lower DC voltage 102. An appropriate range of voltage for safe and efficient operation is between 28-30 volts. In this example, 28 volts is required.

DC voltage 102 flows to DC converter 106, which converts DC voltage 102 to converted voltage 104, usually to a lower voltage. In this example, micro controller 96 and fan 118 require 12 volts of electricity to safely and efficiently operate. Converted voltage 104 travels to micro controller 96 and fan 118.

DC converter 106 sends a signal to switch signal 108 that DC converter 106 is grounded. Switch signal 108 sends a signal to emergency switch 124 that DC converter 106 is grounded. If DC converter 106 or switch signal 108 fails to send a signal that DC converter 106 is grounded, emergency switch 124 shuts down device 10. Emergency switch 124 will shut down device 10 if, for example, several LEDs are shorting out or an optimal operating temperature cannot be maintained. Emergency switch 124 may also be activated manually by an operator.

DC voltage 102 travels to DC relays 112, which receive a signal from micro controller 96 to close the circuits on DC relays 112, sending DC voltage 102 to current monitor 114. DC voltage 102 travels to current monitor 114 and fan controller 116, then to ultraviolet radiation array module 40.

Current monitor 114 monitors voltage used by array module 40. If voltage use is low, current monitor 114 sends a signal to DC relays 112 to output more voltage and from which relay more voltage is needed. If voltage use is high, current monitor 114 sends a signal to DC relays 112 to slow or stop voltage output.

Temperature signal 112 sends information regarding the current temperature of ultraviolet radiation array module 40 to fan controller 116, which sends pulse width modulation 120 to fan 118, to either increase or decrease speed to maintain optimal operating temperature. If fan 118 is not able to maintain optimal operating temperature, fan controller 116 sends a signal to current monitor 114 to shut down DC relays 112. DC voltage 102 stops flowing to DC relays 112. DC converter 106 sends a signal to switch signal 108 that DC converter 106 is no longer grounded. Switch signal 108 sends a signal to emergency switch 124 that DC converter 106 is no longer grounded and emergency switch 124 shuts down device 10.

Micro controller 96 sends relevant information to OLED display 94, which displays information such as overall temperature or current voltage use, for example. An operator may use the information to continue sanitization work or shut down device 10.

An operator depresses finger trigger 92 to emit ultraviolet radiation. Finger trigger 92 sends trigger input 110 to micro controller 96, which sends a signal to DC relays 112 to close the circuits on DC relays 112.

An operator uses slow side-to-side sweeping motions, depressing finger trigger 92 to emit ultraviolet radiation over a first area. After several sweeps, an operator moves to a second area for disinfection, using the same slow side-to-side sweeping motions. The device 10 may be configured as is known in the art so as to indicate to the operator when the required time has passed for exposing a selected surface to the ultraviolet light depending on the surface and the desired level of disinfecting needed.

The beam forming complex 60, is best illustrated in FIGS. 14, 16, 17, and 18. Beam forming complex 60 includes multiple walls 62. Each wall 62 of this embodiment includes a structural base 64 of an appropriate material and a diffuse reflector 66 that is attached to the base 64. As illustrated, the reflector 66 is attached by a pressure sensitive adhesive 68, such as a low surface energy adhesive. A known low surface energy adhesive is made by the 3M Company. In a first embodiment, the reflector is formed of polytetrafluoroethylene (PTFE) and, in particular, may be made of sintered PTFE powder. A preferred embodiment uses 2-3 mm thick sintered PTFE powder sheets. Such sintered PTFE powder sheets are known in the art and are produced commercially, for example, by POREX. Sintered PTFE powder is a preferred configuration to get the maximum reflectivity from PTFE based materials.

The use of a sintered PTFE powder sheet as the surface of the diffuse reflector 66 enables the reflector 66 to work as a beam guide for guiding the ultraviolet light emitted by the LED emitters 44. The PTFE increases reflectively from known conventional reflectors. For example, wherein a polished aluminum parabolic reflector has a reflectivity of around 70%, the PTFE's reflectivity exceeds 90% reflectivity. The reflector 66 of this embodiment is designed to prevent absorption into the frame 50 with the desire to utilize a larger amount of the emission energy from the LED emitters 44 and minimize the amount of ultraviolet light that would be absorbed by the frame 50 if the reflector 66 was formed of a less reflective material. An additional advantage of the PTFE diffuse reflector 66 is that the emission profile is very uniform relative to prior art reflectors or beam shaping designs, which are typically cost prohibitive to achieve similar performance.

Figure 18:
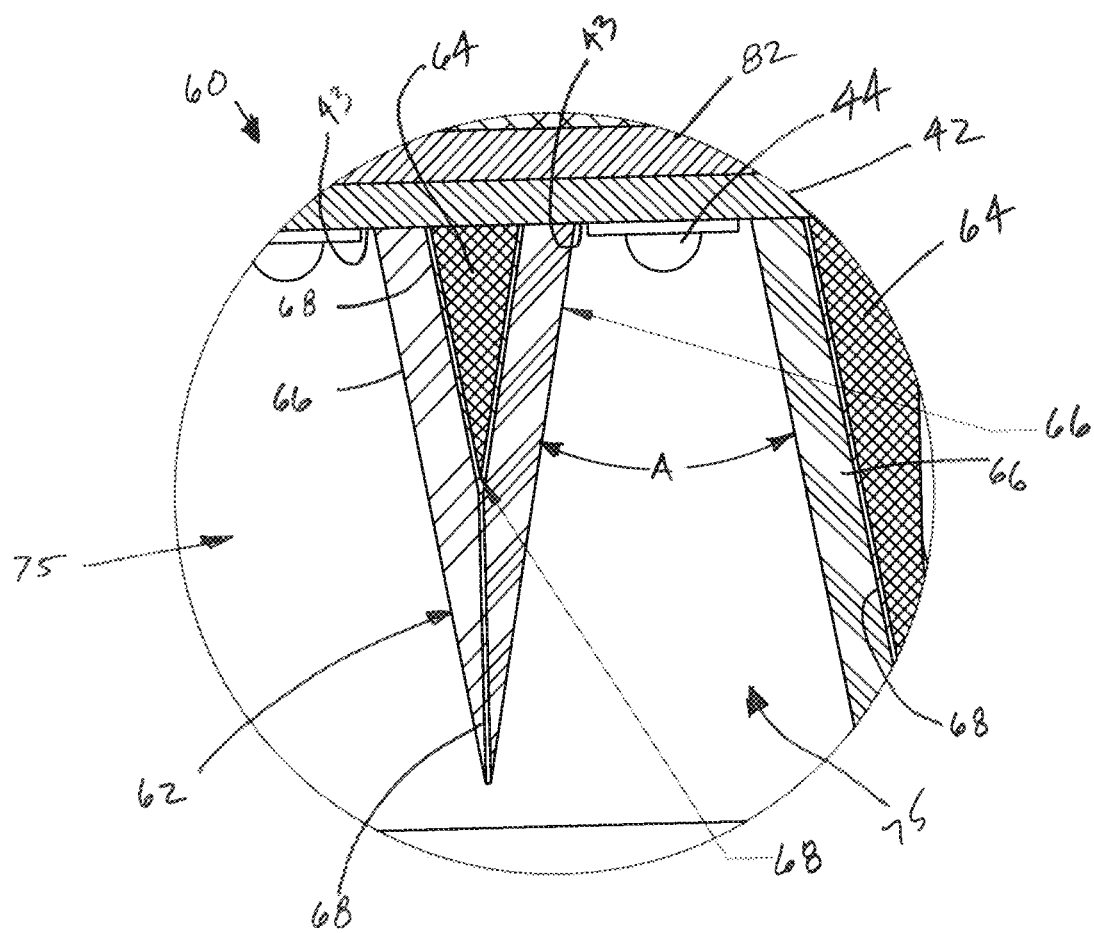
FIG. 18 is an enlarged cross-sectional view of the beam forming walls of the area within the illustrated circular line 18 in FIG. 17.

The walls 62 are formed such that the walls 62 on opposite sides of an LED emitter 44 diverge from each other as the walls 62 extend away from the LED emitter 44. As illustrated in FIGS. 17 and 18, the angle between the diffuse reflector 66 of opposite walls 62 on either side of an LED emitter 44 is an acute angle A (as denoted by the letter A in FIGS. 17 and 18). A preferred acute angle A is approximately 20 degrees, but the angle A will vary to suit the depth 71 of the beam forming complex 60. As illustrated in FIG. 17, the depth 71 of the beam forming complex 60 measures from the LED-engaging surface 43 of the printed circuit board 42 to the lowest edge 73 of the beam forming complex 60. The lowest edge 73 is the part of the beam forming complex 60 that is furthest removed from the LED emitters 44. In the illustrated embodiment, the depth 71 of the beam forming complex is in the range of 0.75 inches to 1.25 inches, while a preferred depth 71 is approximately 0.940 inches. The acute angle A of the reflector 66 combined with the shallow frame depth utilizes the maximum amount of UV-C light transmitted to the surface to be disinfected. As evident in the figures, the walls 62 form a light passageway 75 to direct the ultraviolet light emitted by the LED emitters 44. The light passageway 75 increases in size as the walls 62 diverge from each other.

Figure 19:
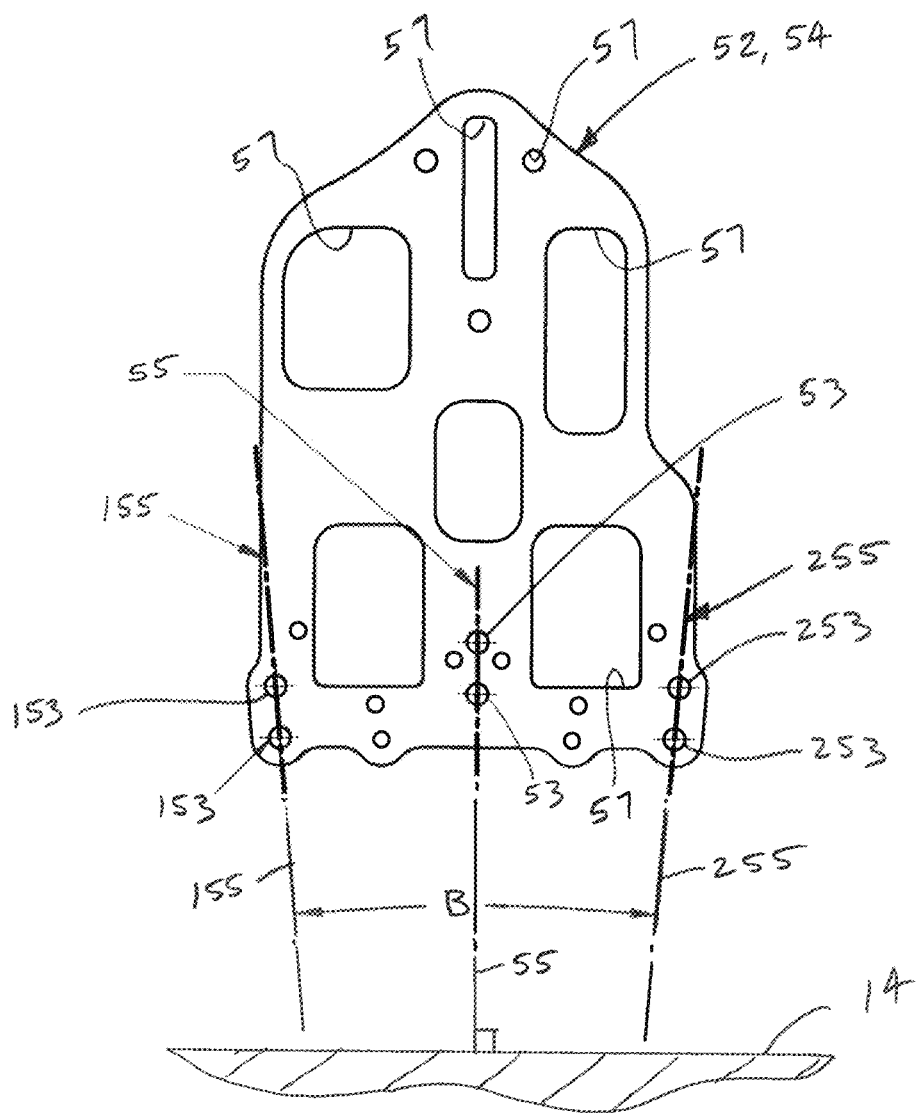
FIG. 19 illustrates an end view of the upright mount in accordance with an embodiment of the invention.

As best seen in FIGS. 8 and 19, the side panels 52 and 54 of frame 50 provide the ability to scale the size of the UV emitter array assembly 30, as will be discussed below. As illustrated side panels 52 and 54 can be made substantially identical and they can be configured to connect to array modules 40 in different ways that enable additional array modules 40 to be connected in a manner that differs from that illustrated in the first embodiment of FIG. 1. In particular, side panels 52, 54 may include single emitter holes 53 that are arranged along a single emitter hole axis 55 that is normal to the surface 14 to be disinfected. The holes 53 are sized and configured to receive appropriate known fasteners to attach the array modules 44 to the side panels 52 and 54. The holes 53 permit the attached array modules 44, including the LED engaging surface 43, to be configured substantially normal to the single emitter hole axis 55. This is illustrated in the first embodiment, as best seen in FIG. 17. As seen in FIG. 19, side panels 52 and 54 also include other openings 57 of various sizes to accommodate and secure other elements of device 10 as mentioned above.

Side panels 52, 54 may also include first double emitter holes 153 that are arranged along a first double emitter hole axis 155 that is not normal to the surface 14 to be disinfected, and second double emitter holes 253 that are arranged along a second double emitter hole axis 255 that is also not normal to the surface 14 to be disinfected. The holes 153 and 253 are sized and configured to receive appropriate fasteners to attach the array modules 44 to the side panels 52 and 54 using conventional fasteners. The holes 153 and 253 permit two rows of array modules 40 to be attached to the side panels 52, 54 instead of just one row of array modules 40 as shown in the previous embodiment illustrated, for example, in FIGS. 16 and 17. Using holes 153 and 253, two rows of array modules may be attached to the side panels 52 and 54 as illustrated in FIGS. 24 and 25, thus allowing the device 10 to be reconfigured into the device 210 with higher ultraviolet light output as illustrated in FIGS. 24 and 25.

As illustrated in FIG. 19, the axes 155 and 255 converge towards each other. The angle between the axes is denoted by the angle B in FIG. 19. Although angle B may be variable to suit the desired intensity of the emitted ultraviolet light, one preferred embodiment is to permit angle B to form an angle of approximately 10 degrees. With the configuration of FIGS. 24 and 25, the attached array modules 44, including the LED engaging surface 43, are configured not to extend normal to the surface 14 to be disinfected but, instead, one row of array modules 40 is configured to extend along the first double emitter hole axis 155 and the other row of array modules 40 is configured to extend along the second double emitter hole axis 255. Thus, the ultraviolet light emitted by the two rows of array modules 40 will contact the surface 14 to be disinfected with converging angles as best seen in FIGS. 19 and 25. As illustrated in FIG. 25, this configuration results in adjacent sides 45 of array modules 44 not being flush and parallel, but to be offset at an angle C from one another. Angle C may be adjusted depending on the desired beam intensity, but a preferred dimension of angle C is approximately 10 degrees plus or minus 5 degrees. The ability to scale the size of the ultraviolet emitter assembly 30, 130 provides the ability to meet the needs in the field. That is, the construction of the frame 50 and its side panels 52, 54, allows for field swapping from a single emitter device 10 with one row of array modules 40 to a double emitter device 210 with two rows of array modules. The fasteners connecting the array modules 40 to the side panels 52, 54 are preferably those of the type that are easily removed either by hand or using tools. Thus a user may disinfect a surface 14 with the single row of array modules 40 as illustrated with respect to device 10 and then remove the single row of array modules 40, rearrange them and reconnect the array modules 40 so as to use the first set of double emitter holes 153, and then add a second row of array modules 40 by connecting the second row of array modules 40 to the second set of double emitter holes 253. Then, the user can use the device 210 and employ an increased emission of ultraviolet light since the number of array modules 40 has doubled. Additionally, since the two rows of array modules 40 are canted towards each other in the double emitter device 210, the ultraviolet beam intensity can be concentrated as desired.

Figure 26:
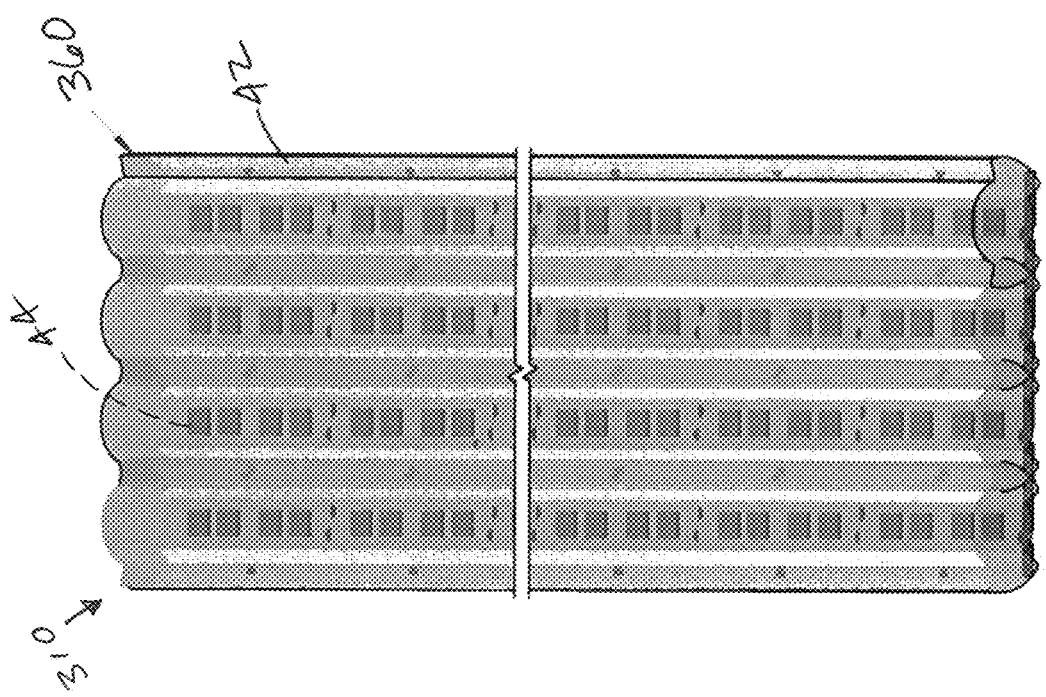
FIG. 26 illustrates a bottom-side perspective view of a beam forming complex in accordance with a second embodiment of the invention.

FIG. 26 shows an additional embodiment of a device 310 that is substantially similar to device 10 but that the beam forming complex 60 of device 10 may be replaced by a total internal reflectance (TIR) lens 360. Such TIR lenses 360 are generally known in the art, although they may be cost prohibitive as TIR lenses 360 are significantly more expensive than the beam forming complex 60 described above.

Figure 27:
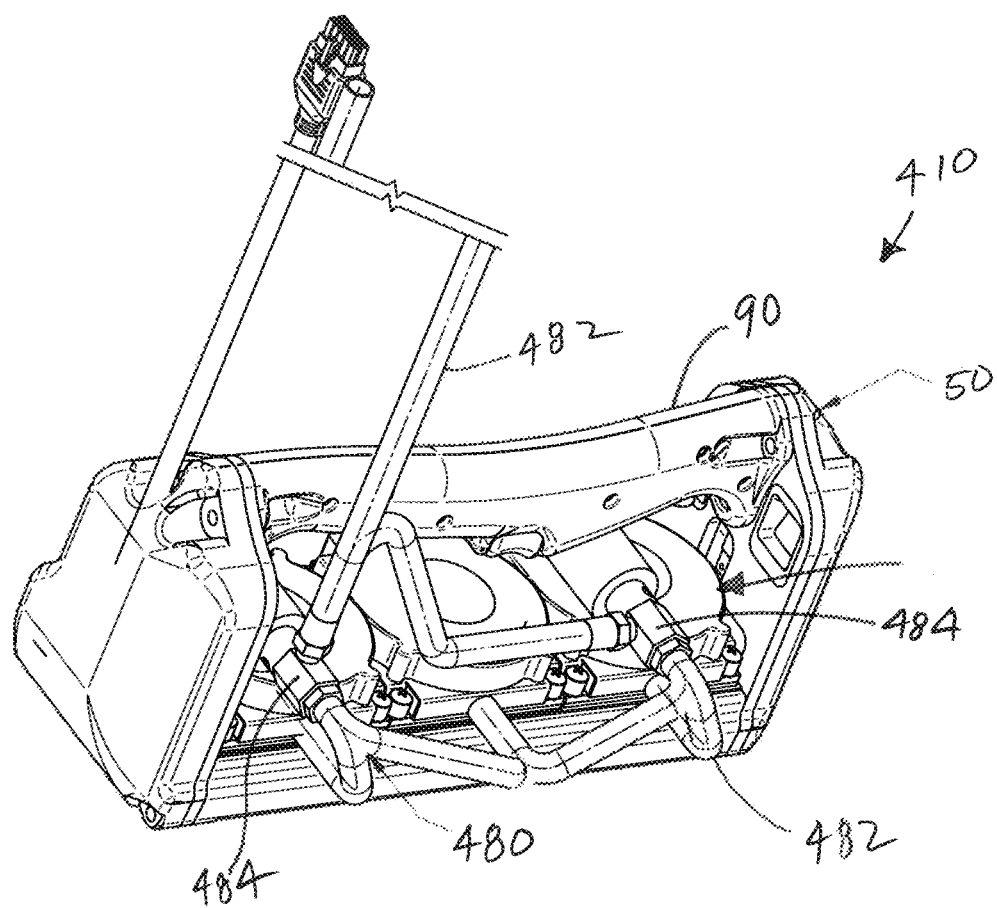
FIG. 27 illustrates a top-side perspective view of the device in accordance with a second embodiment of the invention.

FIG. 27 illustrates yet another embodiment of a device 410 that is substantially similar to device 10, but that the thermal management system 80 of device 10 is replaced with a pneumatic vortex cooler 480. The vortex cooler 480 includes piping 482 and fittings 484 to circulate fluid provided from a fluid source (not shown), as is generally known in the art. Such a change may achieve improved LED emitter performance and unit life by allowing the device 410 to operate at a lower temperature.

Other embodiments are possible. For example, the power supply 20 could include a battery pack to allow for operator flexibility and gain the ability to sterilize surfaces that are in areas that do not have a standard 120 VAC electrical supply.

The present invention, which is disclosed herein, is not to be limited by the embodiments described or illustrated herein, which are given by way of example and not of limitation. Other embodiments of the present invention will be apparent to those skilled in the art from a consideration of the instant disclosure, or from practice of the present invention. Various omissions, modifications, and changes to the principles disclosed herein may be made by one skilled in the art without departing from the true scope and spirit of the present invention, which is indicated by the following claims.

What is claimed is:

1. A device for disinfecting a surface, comprising:
a frame comprising a handle with a trigger, the trigger adapted to control radiation activation via a trigger signal received by a circuit relay;
a power source connected to the frame, the power source adapted to supply power to the circuit relay, the circuit relay electrically connected to a current monitor;
an ultraviolet light emitting array of light emitting diodes connected to the frame, the ultraviolet light emitting array electrically connected to the power source via the current monitor, the current monitor adapted to measure voltage used by the ultraviolet light emitting array, the current monitor adapted to transmit a voltage signal to the circuit relay based on the measured voltage, the ultraviolet light emitting array comprising a printed circuited board housing the light emitting diodes, the printed circuited board having a LED-engaging surface;
a thermal management system comprising a heat extracting device positioned adjacent to and thermally connected to the ultraviolet light emitting array, the thermal management system further comprising a fan, the fan adapted to receive pulse width modulations via a fan controller, the fan controller adapted to receive an operating temperature signal of the ultraviolet light emitting array, wherein the pulse width modulations are based on the operating temperature signal;
a display mounted on the frame, the display adapted to render an emitter temperature based on the operating temperature signal; and,
a beam forming reflector connected to said light emitting array to reflect the ultraviolet light to the surface to be disinfected, said beam forming reflector having two opposing walls on opposite sides of at least one of said light emitting diodes, the two opposing walls of the beam forming reflector comprising a base mounted on the printed circuited board, the beam forming reflector having a depth measured from the LED-engaging surface of the printed circuited board to an edge, each of said two opposing walls extending away from the at least one of said one light emitting diodes in a divergent manner relative to each other such that each of said two opposing walls form a side of an acute angle and, together, said two opposing walls form a light passageway through which the ultraviolet light passes while traveling towards the surface to be disinfected, the acute angle configuration of said two opposing walls widening said light passageway as said light passageway becomes further removed from the at least one of said one light emitting diodes, said two opposing walls being coated with sintered polytetrafluoroethylene, wherein the reflectivity of the beam forming reflector exceeds 90% reflectivity of the ultraviolet light emitted by the at least one of said one light emitting diodes.

2. A device according to claim 1, wherein the handle comprises a gripping surface to be gripped by a user's hand, the trigger connected to the handle to permit the radiation activation by the trigger with by a finger of the user's hand, the trigger adapted to transmit a trigger input to a microcontroller that is adapted to transmit the trigger signal to the circuit relay, the display adapted to further render a sterilization time.

3. A device according to claim 1, wherein the said light emitting diodes are light emitting diodes emitting type-C ultraviolet light.

4. A device according to claim 1, wherein said at least one of said light emitting diodes includes multiple light emitting diodes positioned one next to another in series forming a line of light emitting diodes.

5. A device according to claim 4, wherein said line of light emitting diodes is positioned in between said two opposing walls.

6. A device according to claim 1, wherein each of said two opposing walls has a distal end remote from the at least one of said one light emitting diodes, and the distance from the at least one of said one light emitting diodes to said distal end of each of said two opposing walls is less than two inches in length to improve the effectiveness of ultraviolet light on the surface to be disinfected.

7. A device according to claim 2, wherein the heat extracting device is connected to the frame, the frame comprising a master switch located on a side panel of the frame, the master switch adapted to disarm the device such that the radiation activation by the trigger is prevented, the master switch electrically connected to the power source.

8. A device according to claim 2, wherein the heat extracting device includes the fan, the microcontroller comprising a diagnostic microcontroller adapted to monitor the operating temperature signal of the ultraviolet light emitting array, the diagnostic microcontroller further adapted to transmit the emitter temperature to the display, the fan controller connected to the current monitor and the ultraviolet light emitting array, the fan controller further adapted to transmit a stop signal to the current monitor.

9. A device according to claim 7, wherein said heat extracting device includes a conduit and a fluid within said conduit.

10. A device for disinfecting a surface, comprising:
a frame comprising a handle with a trigger, the trigger adapted to control radiation activation via a trigger signal received by a circuit relay;
a power source connected to the said frame, the power source adapted to supply power to the circuit relay, the circuit relay electrically connected to a current monitor;
first and second ultraviolet light emitting arrays of light emitting diodes connected to the frame and electrically connected to the power source via the current monitor, the first array of light emitting diodes being positioned on a first support that presents h light emitting diodes on a first plane and the second array of light emitting diodes being positioned on a second support that presents the light emitting diodes on a second plane, the current monitor adapted to measure voltage used by the first and second ultraviolet light emitting arrays, the current monitor adapted to transmit a voltage signal to the circuit relay based on the measured voltage, each ultraviolet light emitting array comprising a printed circuited board housing the light emitting diodes, each printed circuited board having a LED-engaging surface;
a thermal management system comprising a heat extracting device positioned adjacent to and thermally connected to the first and second ultraviolet light emitting arrays, the thermal management system further comprising a fan, the fan adapted to receive pulse width modulations via a fan controller, the fan controller adapted to receive an operating temperature signal of the first and second ultraviolet light emitting arrays, wherein the pulse width modulations are based on the operating temperature signal; and,
a first beam forming reflector connected to said first light emitting array and a second beam forming reflector connected to said second light emitting array, each of said first and second beam forming reflectors connected to its respective said light emitting array to reflect the ultraviolet light to the surface to be disinfected, each said beam forming reflector having two opposing walls on opposite sides of at least one of said light emitting diodes, each of the two opposing walls of each beam forming reflector comprising a base mounted on the printed circuited board, each beam forming reflector having a depth measured from the LED-engaging surface of the printed circuited board to an edge, each of said two opposing walls extending away from the at least one of said one light emitting diodes in a divergent manner relative to each other such that each of said two opposing walls form a side of an acute angle and, together, said two opposing walls form a light passageway through which the ultraviolet light passes while traveling towards the surface to be disinfected, the acute angle configuration of said two opposing walls widening said light passageway as said light passageway becomes further removed from the at least one of said one light emitting diodes, said first and second light emitting arrays being connected to said frame such that said first plane forms an acute angle with said second plane such that a first line normal to said first plane will converge with a second line normal to said second plane.

11. A device according to claim 10, wherein said two opposing walls of each of said first and second beam forming reflector are coated with sintered polytetrafluoroethylene, wherein the reflectivity of the beam forming reflector exceeds 90% reflectivity of the ultraviolet light emitted by said light emitting diodes.

12. A device according to claim 10, wherein the handle comprises a gripping surface to be gripped by a user's hand, the trigger connected to the handle to permit the radiation activation by the trigger with a finger of the user's hand.

13. A device according to claim 10, wherein said light emitting diodes are light emitting diodes emitting type-C ultraviolet light.

14. A device according to claim 10, wherein the trigger is adapted to transmit a trigger input to a microcontroller, the microcontroller adapted to transmit the trigger signal to the circuit relay based on the trigger input, the microcontroller further adapted to monitor the operating temperature signal of the ultraviolet light emitting array, the microcontroller also adapted to transmit an emitter temperature to a display based on the operating temperature signal, the display adapted to render the emitter temperature.

15. A device according to claim 10, wherein the fan controller is connected to the current monitor and the ultraviolet light emitting array, the fan controller further adapted to transmit a stop signal to the current monitor, wherein an emergency switch deactivates the device based on the stop signal.

16. A device according to claim 15, wherein the emergency switch comprises a master switch located on a side panel of the frame.

* * * * *